United States Patent [19]

Cooke, Jr.

[11] 4,109,717
[45] Aug. 29, 1978

[54] METHOD OF DETERMINING THE ORIENTATION OF HYDRAULIC FRACTURES IN THE EARTH

[75] Inventor: Claude E. Cooke, Jr., Houston, Tex.

[73] Assignee: Exxon Production Research Company, Houston, Tex.

[21] Appl. No.: 848,067

[22] Filed: Nov. 3, 1977

[51] Int. Cl.² ............................................. E21B 47/06
[52] U.S. Cl. ...................................... 166/250; 73/154
[58] Field of Search ...................... 166/250, 254, 255; 73/154, 362 AR

[56] References Cited

U.S. PATENT DOCUMENTS

| | | | |
|---|---|---|---|
| 2,764,024 | 9/1956 | Rumble | 73/362 AR |
| 3,363,457 | 1/1968 | Ruehle et al. | 73/154 |
| 3,402,769 | 9/1968 | Doggett et al. | 166/254 |
| 3,480,079 | 11/1969 | Guinn et al. | 166/250 |
| 3,745,822 | 7/1973 | Pierce et al. | 73/154 |

Primary Examiner—Stephen J. Novosad
Attorney, Agent, or Firm—Robert L. Graham

[57] ABSTRACT

A method of determining the orientation of fractures in a cased well by determining the temperature differences (and direction thereof) between the circumference and the interior of the well prior to dissipation of the thermal disturbances created by the fracturing treatment.

12 Claims, 6 Drawing Figures

METHOD OF DETERMINING THE ORIENTATION OF HYDRAULIC FRACTURES IN THE EARTH

BACKGROUND OF THE INVENTION

1. Field of the Invention

This invention relates to a method for determining the orientation of hydraulically induced fractures in the earth.

2. Description of the Prior Art

Hydraulic fracturing is a production stimulation technique that has been widely used by the oil industry for several years. In a hydraulic fracturing treatment, fluid is injected down a well and into a subterranean formation at rates and pressure sufficient to crack or fracture the subterranean formation. The earth stresses are almost always such that when the rock fails, a vertical fracture similar to that shown in FIG. 5 will be formed. Continued injection of the fracturing fluid increases the fracture length and width. In order to maintain the fracture open, particulate propping agent is injected into the fracture and deposited therein. The conductivity within the propped fracture is substantially higher than the permeability of the formation which changes the flow pattern of produced fluids from a radial flow pattern to a linear flow pattern thereby increasing the productivity of the well.

Since fractures propagate by displacement of the walls of the fracture, the plane of propagation (and, therefore, the orientation of the fracture) is determined by the orientation of the minimum compressive stress in the vicinity of the fracture tip. The fracture normally extends in a direction perpendicular to the least compressive "far field" stress because of the principle of minimum work. The principal rock stress directions are nearly constant over large areas. Thus, the azimuth of the fracture plane will be almost uniform within any reservoir. Knowledge of the azimuthal orientation of the fracture can be of significant value in several oil field operations, as for example, in the selection of injection and producing wells for secondary recovery, since the fluid flow pattern between wells affects efficiency. Also, in the stimulation of wells near fault boundaries or lease lines and in the stimulation of low permeability gas sands by long hydraulic fractures, it would be useful to know the direction of the fracture.

The orientation of a fracture can be determined by several prior art techniques including 1) the use of inflatable impression packers, 2) pressure pulse testing between wells, 3) use of downhole television. All of these techniques, however, either must be performed in an open hole (the inflatable impression packer, downhole television) or lack accuracy (pressure pulse testing). These factors requiring special treating generally militated against the use of such techniques. For example, the pulse testing technique requires the monitoring of pressures in several surrounding wells and, therefore, is time consuming and expensive.

U.S. Pat. No. 3,745,822 describes a technique for determining fracture orientation but relies on an observation well and the effects of thermal energy from an external source such as an input well.

In summary, there is a need in the industry for a simple and reliable technique for determining the orientation of fractures emanating from a cased wellbores.

SUMMARY OF THE INVENTION

It surprisingly has been discovered that the orientation of a fracture extending from a cased wellbore can be determined by measuring the temperature circumferentially about the interior of said casing proximate to the location of injection prior to but during dissipation of the thermal effects created by the fracturing fluid. The fluid will normally be colder than formation temperature but can be heated to a temperature higher than the formation temperature. The thermal effects caused by the injection of the fluid will be dissipated relatively rapidly in the formation rock, whereas the fluid in the fracture itself will equalize to the formation temperature much more slowly. By measuring the circumferential temperature about the interior of the casing and determining the azimuth of such measurements, the diametrically opposed temperature extremes provide an indication of the fracture orientation.

In one embodiment of the invention, the temperature measurement step is provided by rotating a single probe temperature sensing element in contact with the casing and recording the temperature and direction on the probe at the surface. The temperature sensing element should be quite sensitive, being capable of measuring temperatures in the order of between about 0.01° F and 0.2° F. In another embodiment, the temperature effects are determined by measuring the temperature difference between the inner circumference of the casing and fluid within the casing.

DESCRIPTION OF THE PREFERRED EMBODIMENT

Figure 1:
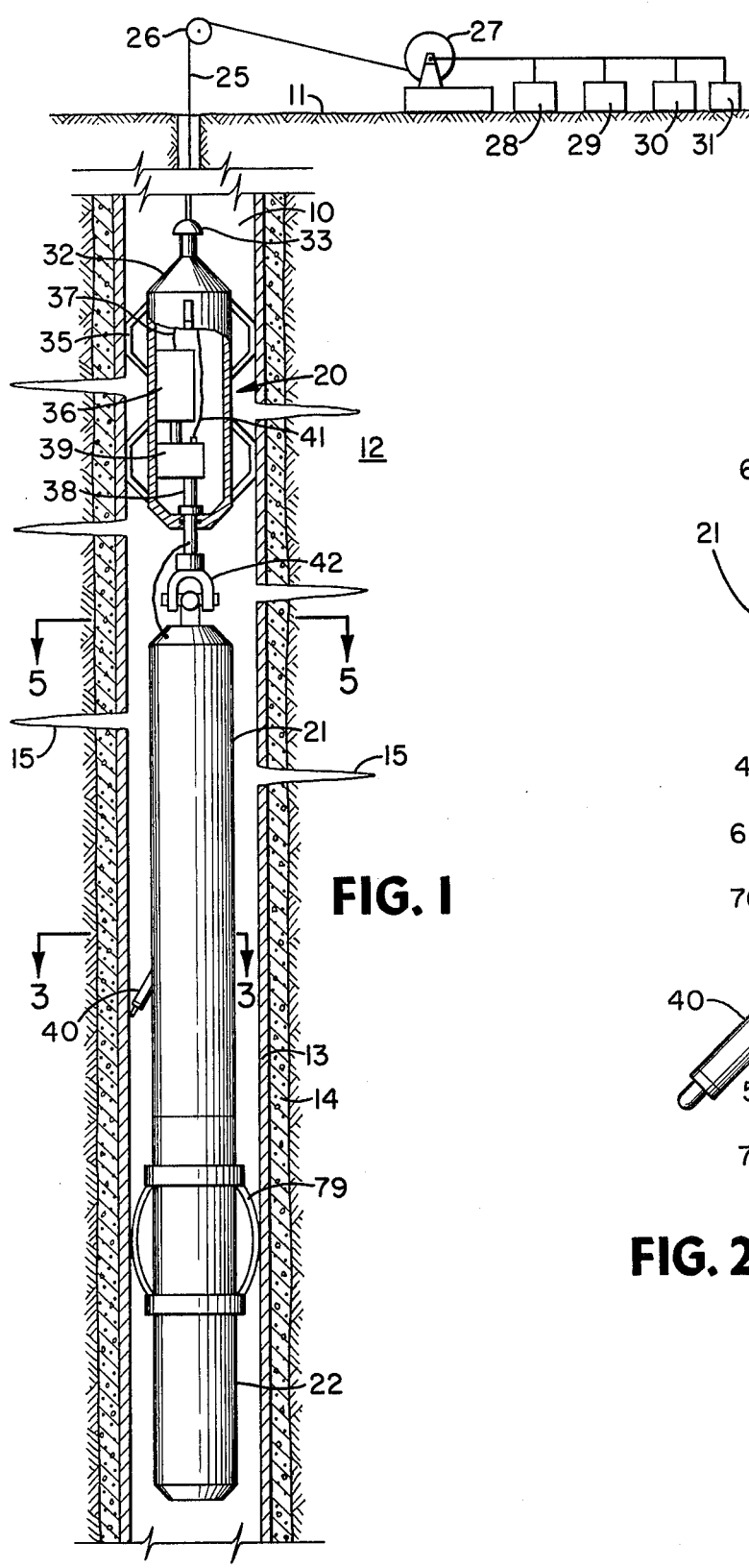
FIG. 1 is a vertical sectional view of a well illustrating one embodiment of apparatus for carrying out the present invention.

Referring to FIG. 1 of the drawings, a well 10 extends from the surface of the earth 11 and penetrates subsurface producing formation 12. (Note that the lower portion of the well in FIG. 1 has been expanded to illustrate details of the apparatus.) A casing string 13 has been introduced into the borehole and cemented in place, providing a cement sheath 14 about the casing 13. Perforations 15 penetrate the casing 13 and sheath 14 providing fluid communication between the formation 12 and well 10.

Figure 3:
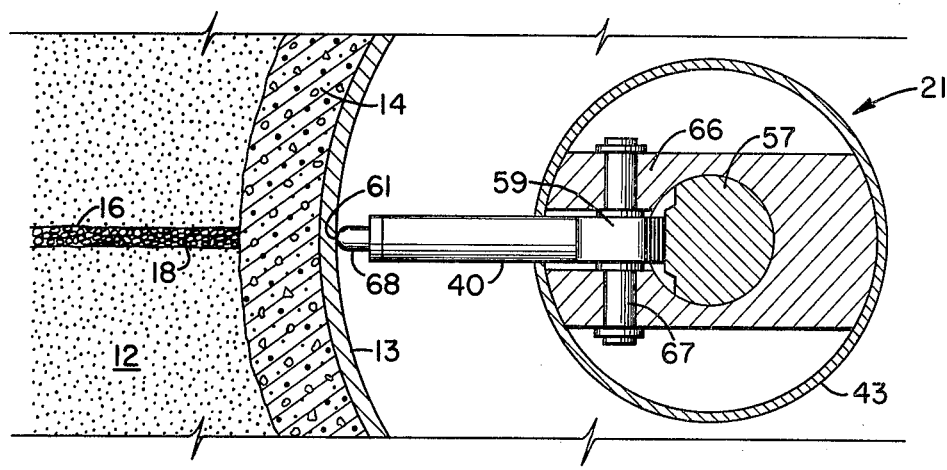
FIG. 3 is a fragmentary cross sectional view of the temperature sensing assembly taken generally along the section 3—3 of FIG. 1 illustrating a probe in contact with the well casing.
Figure 5:
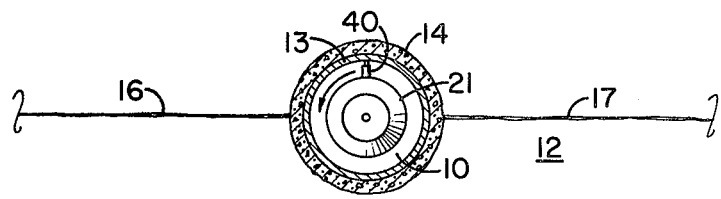
FIG. 5 is a sectional view of the apparatus shown in FIG. 1, the cutting plane taken generally along the section 5—5 thereof.

Stimulation of formation 12 may be achieved by pumping a fracturing fluid down the casing 13 through the perforations 15 and into the formation 12. The properties of the fluid and the pumping rate are such that the injection pressure exceeds the rock stress causing the formation rock to fail in tension. This rock failure almost always results in a vertical fracture extending radially outwardly from the well 180° apart. FIG. 5 illustrates a vertical fracture wherein fracture cracks 16 and 17 extend outwardly from the well 10 in opposite directions. The fracture will normally extend several hundred feet from the well. Particulate propping agent such as frac sand (usually 10/20 mesh or 20/40 mesh in size) is generally used to prop the fracture open. Propping agent particles 18 are illustrated in FIG. 3 as being deposited in the fracture. The performance of the fracturing operation may be in accordance with any one of the several available techniques used in the industry. The fracturing fluids and propping agent as well as the fracturing equipment are described at length in the literature.

DESCRIPTION OF APPARATUS

The three components useful in carrying out the method of determining fracture orientation are lowered in assembled relation into the well 10 on a multiconductor electrical cable 25 (FIG. 1). The three components include a rotator assembly 20, temperature sensor assembly 21, and orientation device 22. The multiconductor cable 25 moves over a suitable pulley 26 at the wellhead and a cable drum 27 raises and lowers the apparatus as desired. Suitable electrical signals from the downhole apparatus are transmitted to the rotator assembly control 28, the temperature sensor motor control 29, the temperature sensor output analyzer 30, and orientation device output analyzer 31.

The rotator assembly 20 is provided with a fishing neck 33 through which the multiconductor cable 25 passes. The rotator housing 32, shown cutaway, has centralizers 35 suitably attached to its external surface to minimize rotation of the exterior of the assembly 20. Mounted within the housing 32 is a reversible electric motor 36 which is powered by the surface motor control 28 through cable 25 and leads 37. The output shaft 38 of motor 36 is connected to a suitable power transmission assembly 39, such as a gear box, and serves to rotate the temperature sensing assembly 21 and orientation device 22.

A cable 41 passes through shaft 38 and electrically interconnects the cable 25 with the temperature sensor assembly 21 and the orientation device 22. The power transmission output shaft 38 of the rotator assembly 20 is connected to the temperature sensing assembly 21 by a suitable flexible joint 42. Thus, when the rotator motor 36 is actuated by the operator at the surface motor control 28, the temperature sensing assembly 21 and orienting device 22 will rotate about the vertical axis. The rotator assembly 20 will tend to remain stationary due to the frictional contact of the centralizers 35 on the casing 13.

Figure 2:
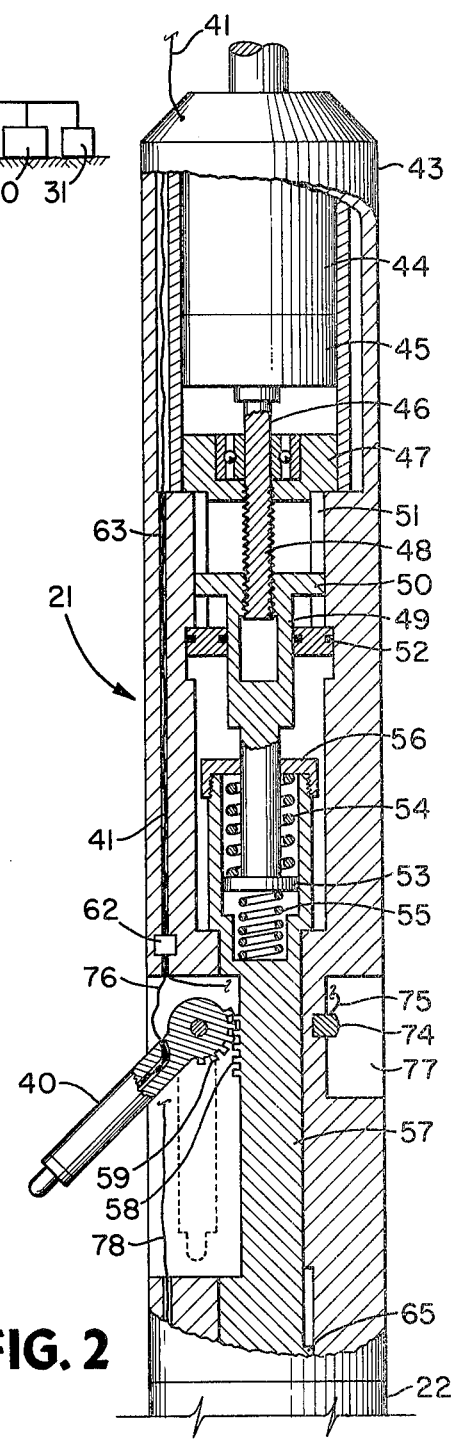
FIG. 2 is a longitudinal sectional view of a portion of the apparatus shown in FIG. 1.

Referring to FIG. 2, the temperature sensing assembly 21 includes a temperature probe 40 and electrically powered transmission means for moving the probe 40 from a retracted, running-in position (broken line position of FIG. 2) to an extended, operating position (solid line position of FIG. 2).

The temperature sensing assembly 21 is provided with a housing 43 which couples at its lower end with the orienting device 22. At the upper end of the housing 43 there is suitable opening through which the multiconductor cable 41 passes. Suitable leads from the multiconductor cable 41 are provided for powering the electrical reversible temperature sensor motor 44 which supplies rotary power to a suitable power transmission 45. The power transmission output shaft 46 is journaled to support 47 and has a threaded lower end 48. A connecting member 49 movably mounted in housing 43 has an internally threaded bore which mates with the threaded end 48 of the power output shaft 46. Keys 50 are provided at the upper end of the connecting member 49 which ride in key slots 51. Thus, rotation of the output shaft 46 causes vertical movement of the connecting member 49 since rotational motion of the member is prevented by keys 50 and 51. Hydraulic seals 52 are provided on the exterior of the connecting member 49 to prevent entry of well fluids into the temperature sensor motor 44 and power transmission 45.

The lower end of connecting member 49 is provided with a flange 53 which bears against opposed compression springs 54 and 55. The springs 54 and 55, housed in the upper end of rack member 57, provide a proper dampening action to movement of the connecting member 49 and prevent overpowering motor 44. The connecting member 49 passes through a suitable central opening in a cap 56 which is threadably connected to the upper end of rack member 57. A rack member 57 is provided with rack threads 58. As the connecting member 49 moves upward due to rotation of the power output shaft 46, spring 54 will compress and bear against the cap 56. This upward force will cause the rack member 57 to move vertically upward and move the probe assembly 40 to its retracted position as shown by the broken lines in FIG. 2 through the action of the sector gear 59 and the rack threads 58. As the connecting member 49 moves down, occasioned by rotation of shaft 46 in the opposite direction, the probe assembly 40 will move to the extended position as shown in FIG. 2 in a similar manner. The lower end of the rack member 57 is provided with a protection stop 65 in a suitable slot to prevent override of the rack and pinion gearing. A similar stop is provided by the abutment of the rack member 57 with the housing 43 at a point above the probe assembly 40.

Figure 4:
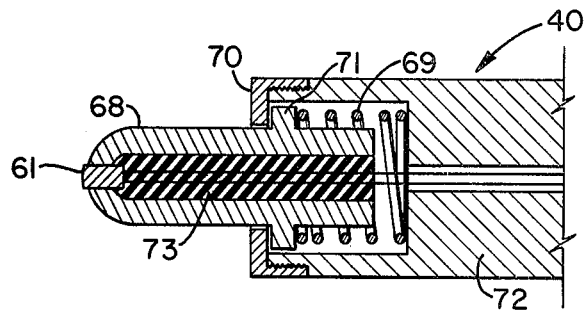
FIG. 4 is a sectional view illustrating details of the probe shown in FIG. 3.

The preferred embodiment of the temperature sensor assembly has one probe assembly 40. As shown in FIGS. 2 and 4, the probe assembly 40 contains a temperature sensor 61, which is electrically connected with an oscillator 62 through lead 76. The temperature sensor 61 may be of the resistance type, such as thermistor; the oscillator 62 is of the resistance controlled pulse type such as the unijunction relaxation type. Variations in the frequency of the oscillator are directly proportional to temperature of sensor 61, and hence proportional to temperature on the casing 13 at the point of contact.

FIG. 3 shows the operating position of probe assembly 40 and the temperature sensor 61. The probe assembly 40 is shown in its extended position on contact with the casing 13. Probe assembly 40 is mounted on the probe assembly yoke 66 by bearing 67 to permit movement between the extended and retracted positions. The yoke 66 is secured to the interior of the housing 43.

As best seen in FIG. 4, the temperature sensor 61 is mounted in the outer end of probe assembly 40 and is contained in housing 68 which must have a high thermal conductivity. The material of housing 68 may be metallic, such as a suitable nickel alloy. A biasing spring 69 forces the housing 68 outward relative to the probe body 72 and assures proper contact of the sensor 61 with the casing 13. The sensor housing 68 is secured to the probe body 72 by cap 70 and flange 71. Temperature sensor 61 is positioned in a central bore in the housing 68 and secured thereto by an electrically insulating potting material 73 having a high thermal conductivity such as an epoxy resin.

As shown in FIG. 2, second temperature sensor 74 is mounted within housing 43 at about the same elevation as probe assembly 40. Sensor 74, like sensor 61, may be of the resistance type, such as a thermistor and is connected to the oscillator 62 by leads 75. Sensor 74 is exposed to fluids within well 10 through window 77 formed in the housing 43. The output from the oscillator 62 is connected via multiconnector cable 41, which passes through one of the slots 63 in the temperature sensor housing 43, through rotator assembly 20, around pulley 26, and to output analyzer 30. In the output analyzer 30, the oscillator output is connected to an input of a counting rate meter. The counting rate meter is connected with a differential amplifier which generates an output signal directly proportional to the frequency of the oscillator 62 and therefore proportional to the temperature differential between sensors 61 and 74. The output of the amplifier may be connected to a recorder, which provides a continuous recorded display of the temperature differential of the sensors.

The orienting device 22 determines the direction (or azimuth) of the hottest and coldest points on the casing 13 as measured by sensors 61 and 74.

A number of devices are commercially available which will perform this orienting function. Some are magnetic devices; others locate a predetermined point on the casing wall which has a known azimuth; some use gyroscopic means. Certain of the devices have internally contained recorders with no surface indicators; others transmit their orientation to the surface through a suitable electric conductor. An example of one suitable device for performing this function is the Gyroscopic Directional Multishot Survey Instrument available under the trade name of "Surwel" from Sperry-Sun Well Surveying Company (see page 5195 of the Composite Catalogue of Oil Field Equipment and Services, 32nd (1976-77) revision, published by World Oil). This device will measure and record its direction or azimuth with respect to time. Since the orientation device 22 is connected to the temperature sensor 21, this measurement and recording will determine the orientation of the temperature sensor 61 during its operation.

The orienting device 22 may be connected by lead 78 which extends from multiconnector 41 through the lower end of temperature sensing apparatus 21 and to the orienting device 22. Lead 78 via conductors 41 and 25 connects to analyzer 31.

In order to ensure that the temperature sensing apparatus remains within the center of the casing 13, a centralizer 79 may be employed on the upper end of the orienting device.

OPERATION

The invention may be carried out by first fracturing the formation. This is accomplished prior to introduction of any of the apparatus shown in FIG. 1 into the well. High pressure pumps are connected to the well and following pressure testing of equipment a viscous fracturing fluid is pumped down the casing at a high rate and pressure. The pressure opposite the perforation 15 increases until the formation is fractured, forming cracks 16 and 17 extending radially away from the well in opposite directions. Continued injection of the frac fluid propogates the cracks farther and farther away from the well. Normally from about 25,000 to 500,000 gallons of frac fluid are used to propogate and generate the fractures. A propping agent carried in the frac fluid is then deposited in the fracture to maintain the fracture walls apart. With this accomplished, the well is normally shut in and the fracturing equipment removed.

The fracturing fluid is usually several degrees colder than the normal temperature of the well. For example, for a 7,000 foot well having a typical thermal gradient of 0.012° F/ft, the formation would have a temperature of about 154° F. Assuming the fracturing fluid is at ambient surface temperature of 75° F, the fluid entering the fracture would have a temperature of about 100° F which is 54° F colder than the formation. The large volume of relatively cold fluid creates a thermal disturbance in the immediate vicinity of the well and in the fracture cracks 16 and 17. When the well is closed in following the fracturing treatment, experience has shown that the temperature of the casing and fluid in the fracture does not equalize for several hours.

The orientation of the fracture may be determined in accordance with the present invention by determining the circumferential direction on the casing that remains coolest.

The method relies on the fact that the circumferential sections of the casing 13 opposite fracture cracks 16 and 17 (FIG. 5) will be cooler than the casing sections opposite the formation rock. The temperature of the formation rock opposite the casing will return to its normal temperature faster than the fluid in the fracture will be heated to the normal formation temperature. Measurement of the circumferential temperature of the casing 13 at an elevation near the zone of injection prior to dissipation of the thermal disturbances will provide an indication of fracture orientation. This may be achieved by use of the apparatus described above.

The apparatus may be run in the well immediately following shut in or one or two days thereafter. It is preferred, however, to run the apparatus within 24 hours from completion of the fracture treatment. Successive runs may be made at different times after the fracturing treatment.

The apparatus is lowered down well 10 on the multiconductor cable 25 to the subsurface formation of interest. The depth to which the apparatus has been lowered can be measured by any convenient means such as a collar locator (not shown) which may be attached to the apparatus or otherwise suspended from the multiconductor cable 25.

As the apparatus is lowered down the well, the probe assembly 40 is in retracted position as shown by the dotted lines in FIG. 2. When the zone of interest has been reached by the apparatus as indicated by the collar log, the probe assembly 40 is moved to the extended position to contact the interior of casing 13. The temperature sensing apparatus preferably is located immediately below or above the perforated interval so that the perforations 15 do not interfere with probe rotation. The probe assembly is extended by actuation of the temperature sensor motor control 21 at the surface by the operator. This actuation causes the rack member 57 to move downward in the manner previously described and pushes the sensor 61 against the casing 13.

Rotation of the temperature sensing apparatus 25 through 360° produces a plot (similar to FIG. 6) of the temperature differences between the casing 13 (sensor 61) and the fluid in well 10 (sensor 74).

Figure 6:
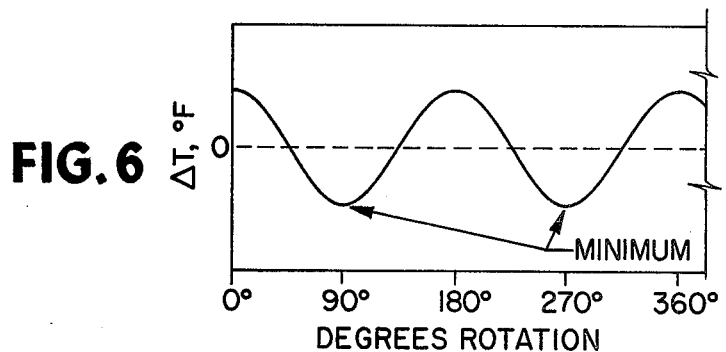
FIG. 6 is a temperature log illustrating a plot of a temperature gradient through 360° rotation of the temperature sensing device shown in FIGS. 1-4.

Assuming the probe 40 rotates counter clockwise as viewed in FIG. 5 and has an initial position as shown, initially the temperature at the circumference will be greater than the temperature of the fluid in the well, as illustrated in FIG. 6. However, as the sensor 61 approaches crack 16, the temperature at the circumference decreases to a value less than the temperature of the fluid in the well, reaching a minimum opposite the crack or after 90° of movement. As the sensor proceeds from crack 16 to crack 17, the temperature at the circumference passes through a second maximum measurement and returns to a second minimum measurement. The minimum measurements will be about 180° apart. Several rotations of the probe may be performed to confirm the minimum points. Correlation of the azimuth of the probe at the minimum measurements determines the orientation of the fracture. This may be achieved by stopping the probe at the minimum temperature difference and observing the azimuth of the orienting device which will be aligned with probe 40.

As a result of these operations the operator can obtain differential temperature measurements and the direction of the minimum or maximum differences on the casing 13.

While the foregoing describes the preferred embodiment of the invention and the best mode of operating that invention, other embodiments are intended to be encompassed by the scope of the invention. For example, the probe assembly need not be extendable and retractable as shown in FIG. 2. The probe assembly could be permanently spring-biased against the walls of the casing in a manner similar to the centralizers 35.

In other embodiments two or three probe assemblies may be used. These assemblies are described in U.S. Pat. No. 3,745,822. Also, a single probe for measuring the direct temperature may be employed. However, due to the small differences in temperature between the casing and the interior of the casing, differential temperature measurements are preferable to direct temperature measurements. For convenience and clarity, both absolute temperatures and differential temperatures are referred to herein collectively as simply "temperatures". In a like manner both types of measurements are referred to as temperature measurements.

Any convenient device for rotating the apparatus of this invention may be used. In lieu of the motor driven device of the preferred embodiment, a hydraulically-actuated device as illustrated in U.S. Pat. No. 3,426,851 or mechanically actuated devices as illustrated in U.S. Pat. No. 2,998,068 or U.S. Pat. No. 3,426,849 might be employed. Also thermal measuring devices other than thermisters may be employed. For example, highly sensitive and accurate thermocouples are commercially available and could be conveniently used.

Variations in the method include using a fluid following the fracturing treatment that has a temperature substantially higher or substantially lower than the formation rock. For example, a hot fluid may be injected to provide greater differences in temperature if necessary.

The present invention may be utilized in connection with conventional operations. The only equipment required is the apparatus illustrated in the drawings. No special fracturing fluids or equipment is needed. The method, therefore, provides a convenient and simple technique for determining orientation of the fracture.

I claim:

1. In a method of stimulating a subterranean formation surrounding a cased wellbore wherein a fluid having a temperature different from the normal temperature of the formation is injected into said formation at a pressure sufficient to form a vertical fracture therein, an improved method for determining the orientation of said fracture which comprises, prior to complete dissipation of the thermal effects created by the injection of the fluid into the formation (a) measuring the circumferential temperature of the interior of the well casing at an elevation proximate said formation and (b) determining direction of temperature extremes so measured, the diametrically opposed temperature extremes indicating the orientation of said fracture.

2. The method as defined in claim 1 wherein said measuring and determining steps are performed within 48 hours from injection of said fluid.

3. The method as defined in claim 2 wherein said step of measuring said circumferential temperature is performed by contacting the interior of said casing with a thermister, rotating said thermister, and recording a continuous plot of said temperature.

4. The method of claim 3 wherein the thermister and associated electronic equipment is capable of measuring a temperature within an accuracy of ±0.01° F.

5. In a method of stimulating a subterranean formation surrounding a cased wellbore wherein a fluid having a temperature different from the normal temperature of said formation is injected into a vertical fracture formed in said formation an improved method for determining the orientation of said fracture which comprises prior to the substantial dissipation of the thermal effects of said fluid, measuring the temperature difference between the circumference of said casing and the fluid within said casing at elevations proximate said formation, determining the direction of the temperature difference measurements, diametrically opposed extremes of said temperature difference measurements providing an indication of said fracture orientation.

6. The method as defined in claim 5 wherein the fluid is colder than the normal subsurface temperature of said formation whereby diametrically opposed minimum temperature differences provide an indication of said fracture orientation.

7. The method as defined in claim 6 wherein the differential temperature is measured by a temperature measuring assembly comprising a first sensor in contact with the interior of said casing, a second sensor disposed within but spaced from said casing, and means for rotating said first sensor.

8. The method as defined in claim 7 wherein said assembly is capable of measuring temperature differentials in the range between about 0.01° F to about 0.2° F.

9. The method as defined in claim 8 wherein the measuring step is performed between about 2 hours and 48 hours after injection of said fluid into said formation and casing.

10. A method of treating a subterranean formation which surrounds a cased well which comprises:
   a. injecting a fluid into said formation to create a vertical fracture therein, said fluid having a temperature colder than the normal temperature of said formation; and
   b. prior to the dissipation of the thermal effects created in the well and formation, determining the direction on the casing that maintains the minimum temperature as the casing and formation temperatures equalize, said direction indicating the orientation of said fracture.

11. In a method of stimulating a subterranean formation surrounding a cased well wherein a fluid having a temperature lower than the normal subsurface temperature of said formation is injected into a vertical fracture in said formation, an improved method for determining the orientation of said fracture which comprises, prior to the substantial dissipation of the thermal effects on said casing created by the injection of said fluid into said formation, rotating a temperature sensor in contact with the casing at an elevation proximate the zone of injection to determine the diametric opposite minimum temperatures on the casing, and determining the azimuthal direction of said minimum temperatures relative to the axis of said well.

12. The method as defined in claim 11 wherein the step of determining the azimuthal direction of said minimum temperatures comprises locating said sensor on said casing at one of said minimum temperatures, and surveying the azimuthal direction of said sensor.

* * * * *